(12) United States Patent
Brown et al.

(10) Patent No.: US 8,129,393 B2
(45) Date of Patent: Mar. 6, 2012

(54) DIARYLMETHYL PIPERAZINE DERIVATIVES, PREPARATIONS THEREOF AND USES THEREOF

(75) Inventors: William Brown, Montreal (CA);
Andrew Griffin, Montreal (CA);
Thomas Hudzik, Wilmington, DE (US);
Carla Maciag, Wilmington, DE (US);
Gennady Smagin, Wilmington, DE (US); Christopher Walpole, Montreal (CA)

(73) Assignee: AstraZeneca AB, Sodertalje (SE)

( * ) Notice: Subject to any disclaimer, the term of this patent is extended or adjusted under 35 U.S.C. 154(b) by 50 days.

(21) Appl. No.: 12/644,309

(22) Filed: Dec. 22, 2009

(65) Prior Publication Data

US 2010/0168130 A1 Jul. 1, 2010

Related U.S. Application Data

(63) Continuation of application No. 11/572,948, filed as application No. PCT/SE2005/001186 on Jul. 27, 2005, now abandoned.

(60) Provisional application No. 60/602,363, filed on Aug. 18, 2004.

(30) Foreign Application Priority Data

Aug. 2, 2004 (SE) ...................... 0401968

(51) Int. Cl.
*A61K 31/497* (2006.01)
*C07D 241/04* (2006.01)

(52) U.S. Cl. ......... 514/255.04; 514/252.12; 514/253.01; 514/253.11; 544/367; 544/370; 544/396

(58) Field of Classification Search ............. 514/255.04, 514/252.12, 253.01, 253.11; 544/367, 370, 544/396
See application file for complete search history.

(56) References Cited

U.S. PATENT DOCUMENTS

| | | |
|---|---|---|
| 3,940,386 A | 2/1976 | Szabo et al. |
| 4,778,789 A | 10/1988 | Fex et al. |
| 5,574,159 A | 11/1996 | Chang et al. |
| 5,658,908 A | 8/1997 | Chang et al. |
| 5,681,830 A | 10/1997 | Chang et al. |
| 5,807,858 A | 9/1998 | Chang et al. |
| 5,840,896 A | 11/1998 | Van Belle et al. |
| 5,854,249 A | 12/1998 | Chang et al. |
| 6,130,222 A | 10/2000 | Roberts et al. |
| 6,680,318 B2 | 1/2004 | Brown et al. |
| 6,680,321 B1 | 1/2004 | Roberts et al. |
| 6,696,447 B2 | 2/2004 | Brown et al. |
| 6,784,181 B2 | 8/2004 | Brown et al. |
| 7,030,124 B2 | 4/2006 | Chang et al. |
| 7,229,994 B2 | 6/2007 | Brown et al. |
| 7,241,764 B2 | 7/2007 | Brown et al. |
| 7,253,173 B2 | 8/2007 | Brown et al. |
| 7,396,834 B2 | 7/2008 | Brown et al. |
| 2004/0138228 A1 | 7/2004 | Roberts et al. |
| 2004/0147526 A1* | 7/2004 | Brown et al. ............ 514/253.01 |
| 2006/0030569 A1 | 2/2006 | Brown et al. |
| 2007/0249619 A1 | 10/2007 | Brown et al. |
| 2007/0254890 A1 | 11/2007 | Brown et al. |
| 2007/0270435 A1 | 11/2007 | Brown et al. |
| 2007/0293502 A1 | 12/2007 | Brown et al. |
| 2008/0262229 A1 | 10/2008 | Brown et al. |

FOREIGN PATENT DOCUMENTS

| | | |
|---|---|---|
| DE | 2431178 | 1/1975 |
| DE | 2900810 | 7/1980 |
| EP | 0133323 | 2/1985 |
| EP | 0166302 | 1/1986 |
| EP | 0283310 | 9/1988 |
| EP | 0289227 | 11/1988 |
| EP | 0624584 | 8/1998 |
| FR | 2696744 | 4/1994 |
| GB | 2076403 | 12/1981 |
| GB | 2210366 | 6/1989 |
| HU | 215847 | 4/1999 |
| HU | 217619 | 3/2000 |
| JP | 7138230 | 5/1995 |
| WO | 8604584 | 8/1986 |

(Continued)

OTHER PUBLICATIONS

Bair et al (Arch Intern Med. 2003;10163(20):2433-45.*

(Continued)

*Primary Examiner* — Brandon Fetterolf
*Assistant Examiner* — Shirley V Gembeh
(74) *Attorney, Agent, or Firm* — Kenneth F. Mitchell

(57) ABSTRACT

Compounds of general formula:

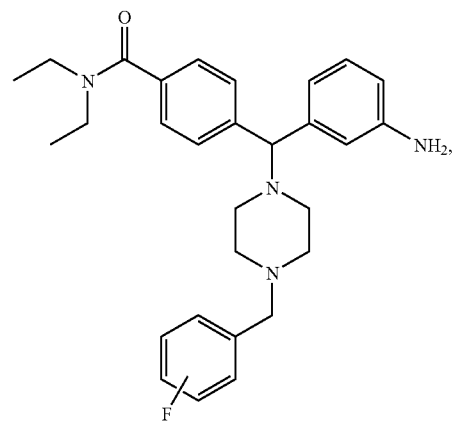

as well as salts, enantiomers thereof and pharmaceutical compositions including the compounds are prepared. They are useful in therapy, in particular in the management of pain, depression and anxiety.

2 Claims, No Drawings

FOREIGN PATENT DOCUMENTS

| WO | 9107967 | 6/1991 |
|---|---|---|
| WO | 9204338 | 3/1992 |
| WO | 9206971 | 4/1992 |
| WO | 9315062 | 8/1993 |
| WO | 9504051 | 2/1995 |
| WO | 9626196 | 8/1996 |
| WO | 9723466 | 7/1997 |
| WO | 9828270 | 7/1998 |
| WO | 9828275 | 7/1998 |
| WO | 9901033 | 1/1999 |
| WO | 9933806 | 7/1999 |
| WO | 0001375 | 1/2000 |
| WO | 0145637 | 6/2001 |
| WO | 0146174 | 6/2001 |
| WO | 0146263 | 6/2001 |
| WO | 0174805 | 10/2001 |
| WO | 02094786 | 11/2002 |
| WO | 02094794 | 11/2002 |
| WO | 02094812 | 11/2002 |
| WO | 03029215 | 4/2003 |
| WO | 03094853 | 11/2003 |
| WO | 2004041800 | 5/2004 |
| WO | 2004041801 | 5/2004 |
| WO | 2004041802 | 5/2004 |
| WO | 2004062562 | 7/2004 |
| WO | 2005066148 | 7/2005 |
| WO | 2006014133 | 2/2006 |
| WO | 2006091160 | 8/2006 |

OTHER PUBLICATIONS

Non-final OA, issued for U.S. Appl. No. 10/714,447 on Sep. 10, 2004.
Final OA issued for U.S. Appl. No. 10/714,447 on Mar. 22, 2005.
Advisory Action issued for U.S. Appl. No. 10/714,447 on Jul. 5, 2005.
Non-final OA, issued for U.S. Appl. No. 10/714,447 on Sep. 9, 2005.
Final OA issued for U.S. Appl. No. 10/714,447 on Feb. 16, 2006.
Non-final OA issued for U.S. Appl. No. 10/477,642 on Jan. 13, 2005.
Non-final OA issued for U.S. Appl. No. 10/477,642 on Jun. 15, 2005.
Final OA issued for U.S. Appl. No. 10/477,642 on Nov. 25, 2005.
Non-final OA issued for 10/477,642 on Apr. 6, 2006.
Notice of Allowance issued for U.S. Appl. No. 10/477,642 on Feb. 1, 2007.
Non-final OA issued for U.S. Appl. No. 10/533,654 on Apr. 25, 2006.
Non-final OA issued for U.S. Appl. No. 10/533,654 on Dec. 1, 2006.
Non-final OA issued for U.S. Appl. No. 10/533,764 on Apr. 17, 2006.
Final OA issued for U.S. Appl. No. 10/533,764 on Oct. 2, 2006.
Advisory Action issued for U.S. Appl. No. 10/533,764 on Jan. 10, 2007.
Non-final OA issued for U.S. Appl. No. 10/533,744 on Jun. 29, 2007.
Final OA issued for U.S. Appl. No. 10/533,744 on Dec. 4, 2007.
Non-final OA issued for U.S. Appl. No. 11/243,623 on Dec. 7, 2005.
Final OA issued for U.S. Appl. No. 11/243,623 on Jun. 12, 2006.
Non-final OA issued for U.S. Appl. No. 11/243,623 on Aug. 29, 2006.
Final OA issued for U.S. Appl. No. 11/243,623 on May 17, 2007.
Non-final OA issued for U.S. Appl. No. 11/243,623 on Sep. 24, 2007.
Non-final OA issued for U.S. Appl. No. 11/243,623 on Jul. 9, 2009.
Examiner's Answer issued for U.S. Appl. No. 11/243,623 on May 27, 2010.
Non-final OA issued for U.S. Appl. No. 11/572,948 on Jun. 9, 2008.
Final Rejection issued for U.S. Appl. No. 11/572,948 on Feb. 24, 2009.
Non-final OA issued for U.S. Appl. No. 11/572,948 on Nov. 16, 2009.
Non-final OA issued for U.S. Appl. No. 11/743,824 on Sep. 10, 2007.
Non-final OA issued for U.S. Appl. No. 11/743,824 on May 21, 2008.
Final Rejection issued for U.S. Appl. No. 11/743,824 on Jan. 27, 2009.
Non-final OA issued for U.S. Appl. No. 11/743,824 on Aug. 21, 2009.
Final Rejection issued for U.S. Appl. No. 11/743,824 on May 14, 2010.
Notice of Allowance issued for U.S. Appl. No. 11/743,824 on Aug. 19, 2010.

Adriaensen et al., Diabetes Metab. Res. Rev. 21(3), 231-240, 2005.
Banker et al., "Modern Pharmaceutics, 3ed," Marcel Dekker, NY, 1996, pp. 451 & 596.
Bilsky et al., "Characterization of Enantioners of (+) BW373U86 and related compounds: highly selective non-peptidic delta opioid agonists," Regulatory Peptides, 54, pp. 25-26, 1994.
Bilsky et al., "SNC 80, A selective, nonpeptidic and systematically active opioid delta agonist," J. Pharmacol. Exper. Ther., 273: 359-366, 1995.
Burkey et al., "The efficacy of delta-opioid receptor-selective drugs," Medline Abstract for Life Sci. 62:1531-1536, 1998.
Calderon et al., "Probes for narcotic receptor mediated phenomena. 19. Synthesis of . . . opioid receptor agonist," J. Med Chem. 37, pp. 2125-2128, 1994.
Calderson et al., "Probes for narcotic receptor mediated phenomena. 23. Synthesis of . . . opioid receptor ligands," J. Med. Chem. 40, 695-704, 1997.
Chang et al., "A novel, potent and selective nonpeptidic delta opioid receptor agonist BW373U86," J. Pharmacol. And Exper. Ther., 267:852-857, 1993.
Davis et al. Lancet Oncol. 6(9), 696-704, 2005.
Filliol et al., "Mice deficient for delta and mu-opioid receptors exhibit opposing alternations of emotional responses," Nature Genetics, vol. 25, pp. 195-200, 2000.
Greene, "Protective Groups in Organic Synthesis," John Wiley & Sons, 2nd Edition, pp. 267-268 & 331, 1981.
Katrizky et al., "Benzotriazole-mediated arylalkylation and heteroarylalkylation," Chem. Soc. Rev. 23:363-373, 1994.
Kingsbury et al., "Synthesis of structural analogs of leukotriene B and their receptor binding activity," J. Med Chem. 36:3308-3320, 1993.
Lopez et al., "Exploring the structure-activity relationships . . . opioid receptor nonpeptide agonist ligand," J. Med. Chem., 42:5359-5368, 1999.
Nagase et al., "The pharmacological profile of delta opioid receptor ligands, (+) and (−) TAN-67 on pain modulation," Medline for Life Sci. 68:2227-2231, 2001.
Nortey et al., "Piperazinyl benzamidines: synthesis and affinity for the delta opioid receptor," Bioorganic & Medicinal Chemistry letters, vol. 11, pp. 1741-1743, 2001.
Plobeck et al., "New diarylmethylpiperazines as potent and selective nonpeptidic opioid . . . with increased in vitro metabolic stability," J. Med. Chem. 43:3878-3894, 2000.
Przewlocki et al., Curr. Pharm. Des. 11(23), 2941-2943, 2005.
Saitoh., "Potential anxiolytic and antidepressant-like activities of SNC80, a selective delta-opioid agonist, in behavioral models in rodents," J. Pharmacol. Sci., 2004, 95; 374-380.
Snyder et al., "Historical review: opioid receptors," Trends in Pharmacological Sciences, vol. 24, pp. 198-205, 2003.
Suggs et al., "Facile synthesis of 8-substituted quinolines," J. Org. Chem. 45:1514-1515, 1980.
Takemori et al., "Selective natrexone-derived opioid receptor antagonists," Annu. Rev. Pharmaco. Toxico. 32-51: 239-269, 1992.
Vippagunta et al., Advanced Drug Delivery Reviews, 48:3-26, 2001.
West, "Solid State Chemistry and its Applications," Wiley, NY, 1988, pp. 358 & 365.
Wolff, "Burger's Medicinal Chemistry, 5ed, Part 1," John Wiley & Sons, 1995, pp. 975-977.
Zhang et al., "Probes for narcotic receptor mediated phenomena. 26. synthesis . . . opioid receptor ligands," J. Med. Chem.. 42:5455-5463, 1999.
Barn et al., "Synthesis of Novel Analogues of the Delta Opioid Ligand SNC-80 Using AICI3-Promoted Aminolysis," Bioorganic & Medicinal Chemistry Letters, 1999, vol. 9, pp. 1329-1334.
Furness et al., "Probes for Narcotic Receptor-Mediated Phenomena. 27. Synthesis and Pharmacological Evaluation of Selective Delta-Opioid Receptor Agonists from 4-[(alphaR)-alpha-(2S,5R)-4-Substituted-2,5-dimethyl-1-piperazinyl-3-methoxybenzyl]-N,N-diethylbenzamides and their Enantiomers," J. Med. Chem., 2000, vol. 43, pp. 3193-3196.

Brandt et al., "Antinociceptive Effects of Delta-Opioid Agonists in Rhesus Monkeys: Effects on Chemically Induced Thermal Hypersensitivity," The Journal of Pharmacology and Experimental Therapeutics, 2001, vol. 296, No. 3, pp. 939-946.

Patani et al., "Bioisosterism: A Rational Approach in Drug Design," 1996, Chem. Rev., vol. 96, pp. 3147-3176.

Dantzman et al., "Strategies employed and outcomes of the multi-parameter optimization of 4-piperidin-4-ylidenemethyl-benzamides as potent and selective Delta-Opioid Receptor Agonists" Aug. 25, 2010, 240th ACS National Meeting, Boston, MA.

Dantzman, "Strategies employed and outcomes of the multi-parameter optimization of 4-piperidin-4-ylidenemethyl-benzamides as potent and selective Delta-Opioid Receptor Agonists" Jun. 14, 2010.

Griffin et al., "Delta agonist hydroxy bioisosteres: the discovery of 3((1-benzylpiperidin-4-y1)(4-[(diethylamino) carbonyl]phenyl}amino)benzamide with improved delta agonist activity and in vitro metabolic stability" Sep. 22, 2009, Bioorg Med Chem Lett., 19(21):5999-6003.

Jones et al., "N,N-Diethyl-4-[(3-hydroxyphenyl)(piperidin-4-yl)amino] benzamide derivatives: The development of diaryl amino piperidines as potent delta opioid receptor agonists with in vivo anti-nociceptive activity in rodent models," Bioorg. Med. Chem. Lett., 2009, 19 (21), 5994.

English abstract of DE 2900810, Jan. 11, 1979.

Eng abstract of FR 2696744, Oct. 12, 1992.

* cited by examiner

DIARYLMETHYL PIPERAZINE DERIVATIVES, PREPARATIONS THEREOF AND USES THEREOF

CROSS-REFERENCE TO RELATED APPLICATIONS

This application is a continuation of U.S. application Ser. No. 11/572,948, filed Jan. 30, 2007, now abandoned, which is a US National Stage under 35 U.S.C. §371 of International Application No. PCT/SE2005/001186, filed Jul. 27, 2005, which claims priority under 35 U.S.C. §119 (a)-(d) to Swedish application no. 0401968-3, filed Aug. 2, 2004, and 35 U.S.C. §119 (e) to U.S. provisional application No. 60/602,363, filed Aug. 18, 2004, which are all hereby incorporated herein by reference.

FIELD OF THE INVENTION

The present invention is directed to novel compounds, to a process for their preparation, their use and pharmaceutical compositions comprising the novel compounds. The novel compounds are useful in therapy, and in particular for the treatment of pain, anxiety and functional gastrointestinal disorders.

BACKGROUND OF THE INVENTION

The delta ("δ") receptor has been identified as having a role in many bodily functions such as circulatory and pain systems. Ligands for the δ receptor may therefore find potential use as analgesics, and/or as antihypertensive agents. Ligands for the δ receptor have also been shown to possess immunomodulatory activities.

The identification of at least three different populations of opioid receptors (μ, δ and κ) is now well established and all three are apparent in both central and peripheral nervous systems of many species including man. Analgesia has been observed in various animal models when one or more of these receptors has been activated.

With few exceptions, currently available selective opioid δ ligands are peptidic in nature and are unsuitable for administration by systemic routes. One example of a non-peptidic δ-agonist is SNC80 (Bilsky E. J. et al., Journal of Pharmacology and Experimental Therapeutics, 273(1), pp. 359-366 (1995)).

Many δ agonist compounds that have been identified in the prior art have many disadvantages in that they suffer from poor pharmacokinetics and are not analgesic when administered by systemic routes. Also, it has been documented that many of these δ agonist compounds show significant convulsive effects when administered systemically.

PCT Publication WO02/094794 describes some δ-agonists.

However, there is still a need for improved δ-agonists.

DESCRIPTION OF THE INVENTION

We have now surprisingly found that certain compounds exhibit one or more improved properties, i.e. improved δ agonist potency, in vivo potency, pharmacokinetics, bioavailability, in vitro stability, in vivo stability, brain penetration, and/or lower toxicity.

Unless specified otherwise within this specification, the nomenclature used in this specification generally follows the examples and rules stated in *Nomenclature of Organic Chemistry, Sections A, B, C, D, E, F, and H*, Pergamon Press, Oxford, 1979, which is incorporated by references herein for its exemplary chemical structure names and rules on naming chemical structures. Optionally, a name of a compound may be generated using a chemical naming program: ACD/ChemSketch, Version 5.09/September 2001, Advanced Chemistry Development, Inc., Toronto, Canada.

"Enantiomerically pure" refers to a compound containing at least 75% of the named enantiomer out of the total amount of the two possible enantiomers contained therein. In a particular embodiment, "enantiomerically pure" refers to a compound containing at least 90% of the named enantiomer out of the total amount of the two possible enantiomers contained therein. In a more particular embodiment, "enantiomerically pure" refers to a compound containing at least 95% of the named enantiomer out the total amount of the two possible enantiomers contained therein.

"Warm-blooded animal" includes human.

In one aspect, the invention provides a compound of formula I, pharmaceutically acceptable salts thereof, solvates thereof, prodrugs thereof, diastereomers thereof, one or more enantiomers thereof, and mixtures thereof:

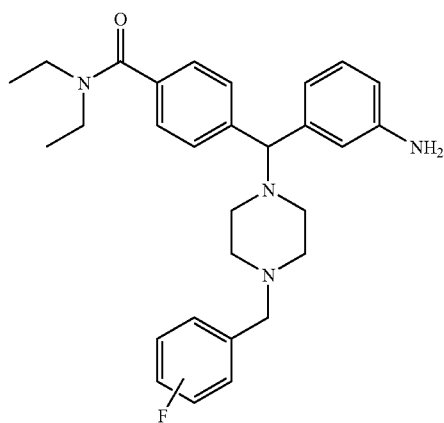

I

In one embodiment, the compound of the invention may be selected from:

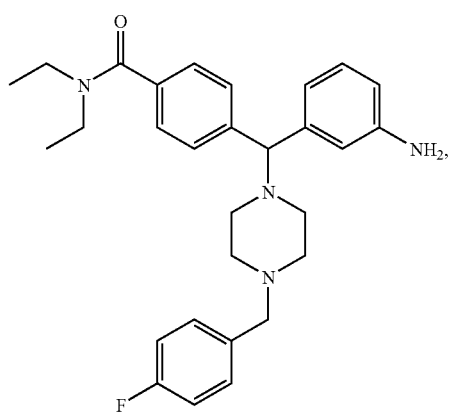

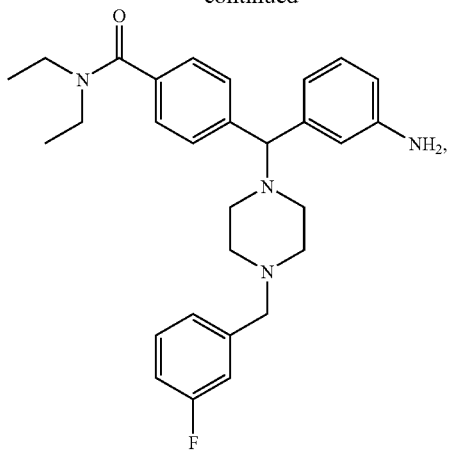

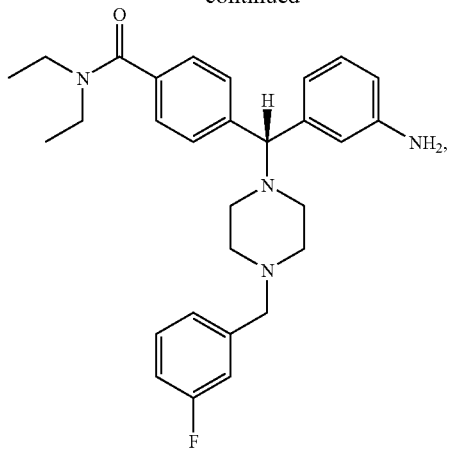

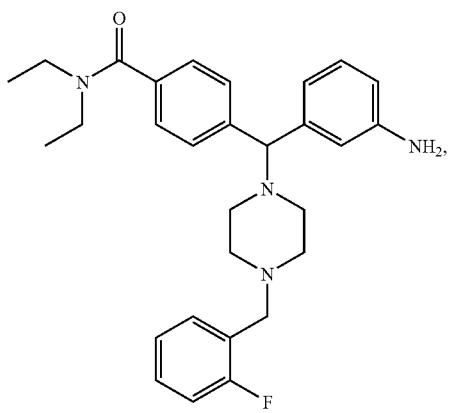

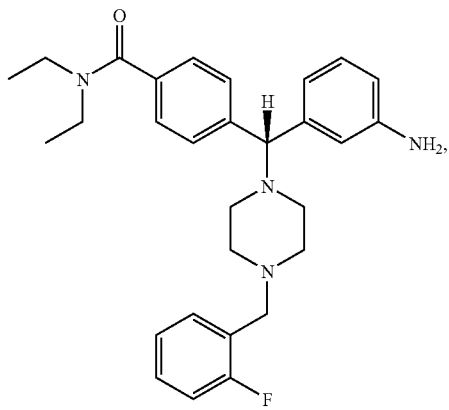

pharmaceutically acceptable salts thereof, one or more isolated enantiomers thereof and mixtures thereof.

In another embodiment, the compound of the invention may be selected from:

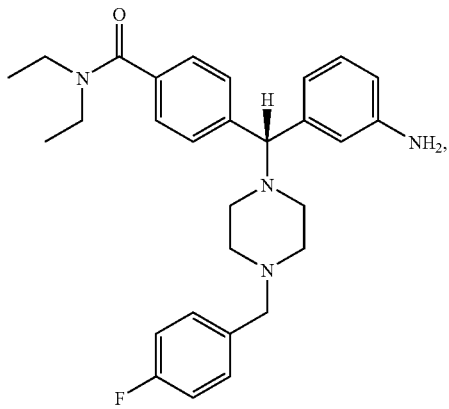

and pharmaceutically acceptable salts thereof.

In a further embodiment, the compound of the present invention may be selected from:

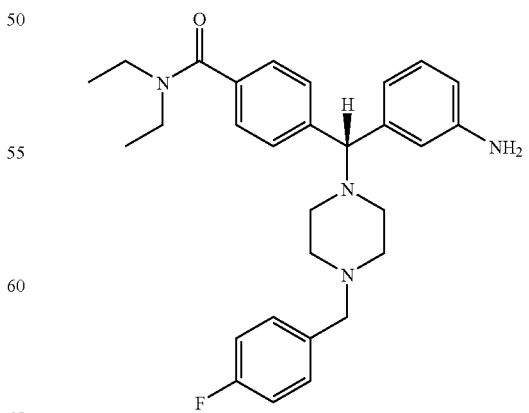

and pharmaceutically acceptable salts thereof.

In a further embodiment, the compound of the present invention may be selected from:

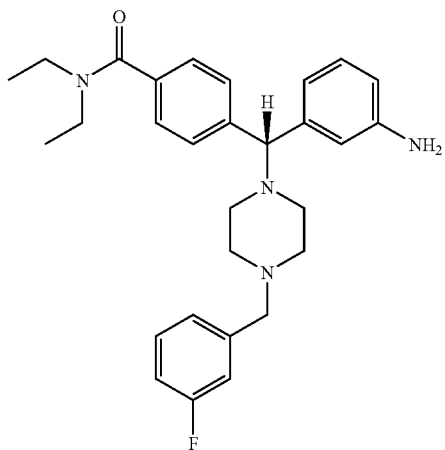

and pharmaceutically acceptable salts thereof.

In a further embodiment, the compound of the present invention may be selected from:

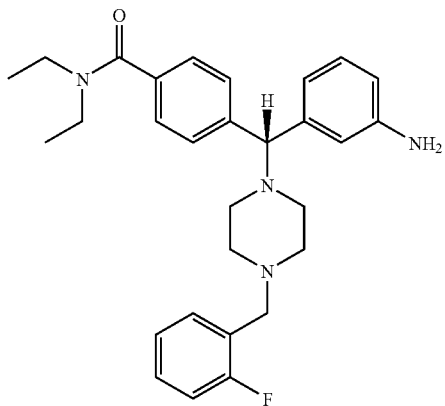

and pharmaceutically acceptable salts thereof.

In a further embodiment, the compound of the present invention may be selected from 4-{(S)-(3-aminophenyl)[4-(4-fluorobenzyl)piperazin-1-yl]methyl}-N,N-diethylbenzamide; 4-{(R)-(3-aminophenyl)[4-(4-fluorobenzyl)piperazin-1-yl]methyl}-N,N-diethylbenzamide; 4-[(R)-(3-aminophenyl)[4-[(2-fluorophenyl)methyl]-1-piperazinyl]methyl]-N,N-diethylbenzamide; 4-[(R)-(3-aminophenyl)[4-[(3-fluorophenyl)methyl]-1-piperazinyl]methyl]-N,N-diethyl-benzamide and pharmaceutically acceptable salts thereof.

In an even further embodiment, the compound of the present invention may be selected from enantiomerically pure 4-{(S)-(3-aminophenyl)[4-(4-fluorobenzyl)piperazin-1-yl]methyl}-N,N-diethylbenzamide; enantiomerically pure 4-{(R)-(3-aminophenyl)[4-(4-fluorobenzyl)piperazin-1-yl]methyl}-N,N-diethylbenzamide; enantiomerically pure 4-[(R)-(3-aminophenyl)[4-[(2-fluorophenyl)methyl]-1-piperazinyl]methyl]-N,N-diethylbenzamide; enantiomerically pure 4-[(R)-(3-aminophenyl)[4-[(3-fluorophenyl)methyl]-1-piperazinyl]methyl]-N,N-diethylbenzamide and pharmaceutically acceptable salts thereof.

It will be understood that when compounds of the present invention contain one or more chiral centers, the compounds of the invention may exist in, and be isolated as, enantiomeric or diastereomeric forms, or as a racemic mixture. The present invention includes any possible enantiomers, diastereomers, racemates or mixtures thereof, of a compound of Formula I. The optically active forms of the compound of the invention may be prepared, for example, by chiral chromatographic separation of a racemate, by synthesis from optically active starting materials or by asymmetric synthesis based on the procedures described thereafter.

It will also be understood that certain compounds of the present invention may exist in solvated, for example hydrated, as well as unsolvated forms. It will further be understood that the present invention encompasses all such solvated forms of the compounds of the formula I.

Within the scope of the invention are also salts of the compounds of the formula I. Generally, pharmaceutically acceptable salts of compounds of the present invention may be obtained using standard procedures well known in the art, for example by reacting a sufficiently basic compound, for example an alkyl amine with a suitable acid, for example, HCl or acetic acid, to afford a physiologically acceptable anion. It may also be possible to make a corresponding alkali metal (such as sodium, potassium, or lithium) or an alkaline earth metal (such as a calcium) salt by treating a compound of the present invention having a suitably acidic proton, such as a carboxylic acid or a phenol with one equivalent of an alkali metal or alkaline earth metal hydroxide or alkoxide (such as the ethoxide or methoxide), or a suitably basic organic amine (such as choline or meglumine) in an aqueous medium, followed by conventional purification techniques.

In one embodiment, the compound of formula I above may be converted to a pharmaceutically acceptable salt or solvate thereof, particularly, an acid addition salt such as a hydrochloride, hydrobromide, phosphate, acetate, fumarate, maleate, tartrate, citrate, methanesulphonate or p-toluenesulphonate.

The novel compounds of the present invention are useful in therapy, especially for the treatment of various pain conditions such as chronic pain, neuropathic pain, acute pain, cancer pain, pain caused by rheumatoid arthritis, migraine, visceral pain etc. This list should however not be interpreted as exhaustive.

Compounds of the invention are useful for the treatment of diarrhoea, depression, anxiety and/or stress-related disorders such as post-traumatic stress disorders, panic disorder, generalized anxiety disorder, social phobia, and obsessive compulsive disorder, urinary incontinence, premature ejaculation, various mental illnesses, cough, lung oedema, various gastro-intestinal disorders, e.g. constipation, functional gastrointestinal disorders such as Irritable Bowel Syndrome and Functional Dyspepsia, Parkinson's disease and other motor disorders, traumatic brain injury, stroke, cardioprotection following miocardial infarction, spinal injury and drug addiction, including the treatment of alcohol, nicotine, opioid and other drug abuse and for disorders of the sympathetic nervous system for example hypertension.

Compounds of the invention are useful as immunomodulators, especially for autoimmune diseases, such as arthritis, for skin grafts, organ transplants and similar surgical needs, for collagen diseases, various allergies, for use as anti-tumour agents and anti viral agents.

Compounds of the invention are useful in disease states where degeneration or dysfunction of opioid receptors is present or implicated in that paradigm. This may involve the use of isotopically labelled versions of the compounds of the invention in diagnostic techniques and imaging applications such as positron emission tomography (PET).

Compounds of the invention are useful as an analgesic agent for use during general anaesthesia and monitored anaesthesia care. Combinations of agents with different properties are often used to achieve a balance of effects needed to maintain the anaesthetic state (e.g. amnesia, analgesia, muscle relaxation and sedation). Included in this combination are inhaled anaesthetics, hypnotics, anxiolytics, neuromuscular blockers and opioids.

Within the scope of the invention is the use of any compound of formula I as defined above for the manufacture of a medicament.

Also within the scope of the invention is the use of any compound of the invention for the manufacture of a medicament for the therapy of pain including, but not limited to: acute pain, chronic pain, neuropathic pain, back pain, cancer pain, and visceral pain.

Also within the scope of the invention is the use of any compound of the invention for the manufacture of a medicament for the therapy of anxiety, including, but not limited to: social phobia, general anxiety disorder, acute anxiety.

Also within the scope of the invention is the use of any compound of the invention for the manufacture of a medicament for the therapy of depression.

Also within the scope of the invention is the use of any compound of the invention for the manufacture of a medicament for the therapy of Parkinson's disease.

Also within the scope of the invention is the use of any of the compounds of the present invention, for the manufacture of a medicament for the treatment of any of the conditions discussed above.

A further aspect of the invention is a method for the treatment of a subject suffering from any of the conditions discussed above, whereby an effective amount of a compound of the present invention, is administered to a patient in need of such treatment.

Thus, the invention provides a compound of formula I, or pharmaceutically acceptable salt or solvate thereof, as hereinbefore defined for use in therapy.

In the context of the present specification, the term "therapy" also includes "prophylaxis" unless there are specific indications to the contrary. The term "therapeutic" and "therapeutically" should be construed accordingly. The term "therapy" within the context of the present invention further encompasses to administer an effective amount of a compound of the present invention, to mitigate either a pre-existing disease state, acute or chronic, or a recurring condition. This definition also encompasses prophylactic therapies for prevention of recurring conditions and continued therapy for chronic disorders.

In use for therapy in a warm-blooded animal such as a human, the compound of the invention may be administered in the form of a conventional pharmaceutical composition by any route including orally, intramuscularly, subcutaneously, topically, intranasally, intraperitoneally, intrathoracially, intravenously, epidurally, intrathecally, intracerebroventricularly and by injection into the joints.

In one embodiment of the invention, the route of administration may be orally, intravenously or intramuscularly.

The dosage will depend on the route of administration, the severity of the disease, age and weight of the patient and other factors normally considered by the attending physician, when determining the individual regimen and dosage level at the most appropriate for a particular patient.

Additionally, there is provided a pharmaceutical composition comprising a compound of the present invention, solvates thereof, or a pharmaceutically acceptable salt thereof, in association with a pharmaceutically acceptable carrier.

Particularly, there is provided a pharmaceutical composition comprising a compound of the present invention, solvates thereof, or a pharmaceutically acceptable salt thereof, in association with a pharmaceutically acceptable carrier for therapy, more particularly for therapy of pain and anxiety.

Further, there is provided a pharmaceutical composition comprising a compound of the present invention, solvates thereof, or a pharmaceutically acceptable salt thereof, in association with a pharmaceutically acceptable carrier use in any of the conditions discussed above.

For preparing pharmaceutical compositions from the compounds of this invention, inert, pharmaceutically acceptable carriers can be either solid and liquid. Solid form preparations include powders, tablets, dispersible granules, capsules, cachets, and suppositories.

A solid carrier can be one or more substances, which may also act as diluents, flavoring agents, solubilizers, lubricants, suspending agents, binders, or table disintegrating agents; it can also be an encapsulating material.

In powders, the carrier is a finely divided solid, which is in a mixture with the finely divided compound of the invention, or the active component. In tablets, the active component is mixed with the carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture in then poured into convenient sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term composition is also intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Depending on the mode of administration, the pharmaceutical composition will preferably include from 0.05% to 99% w (percent by weight), more preferably from 0.10 to 50% w, of the compound of the invention, all percentages by weight being based on total composition.

A therapeutically effective amount for the practice of the present invention may be determined, by the use of known criteria including the age, weight and response of the individual patient, and interpreted within the context of the disease which is being treated or which is being prevented, by one of ordinary skills in the art.

In a further aspect, the present invention provides a method of preparing the compounds of the present invention.

In one embodiment, the invention provides a process for preparing a compound of formula I, comprising:

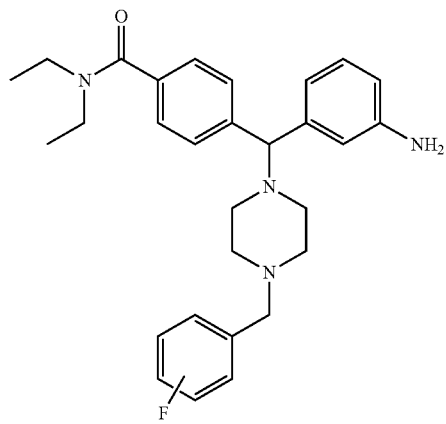

I

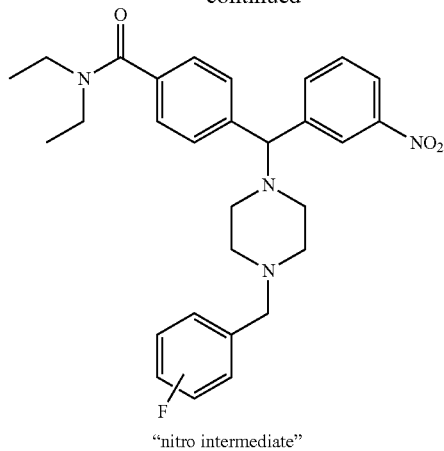

"nitro intermediate"

reacting N,N-diethyl-4-[(3-nitrophenyl)(1-piperazinyl)methyl]benzamide with R—CH$_2$X or R—CHO to form a nitro intermediate compound;

reducing said intermediate compound with a suitable reducing agent, wherein

R is selected from 2-fluorophenyl, 3-fluorophenyl and 4-fluorophenyl; and X is selected from Cl, I, Br, —OTs (tosyl) and —OMs (mesylate).

In one embodiment, said reducing agent may be selected from hydrogen, zinc and iron.

In another embodiment, said N,N-diethyl-4-[(3-nitrophenyl)(1-piperazinyl)methyl]benzamide may be selected from N,N-diethyl-4-[(S)-(3-nitrophenyl)(1-piperazinyl)methyl]benzamide and N,N-diethyl-4-[(R)-(3-nitrophenyl)(1-piperazinyl)methyl]benzamide.

In a further embodiment, R may be 2-fluorophenyl; and the compound of formula I may be 4-[(3-aminophenyl)[4-[(2-fluorophenyl)methyl]-1-piperazinyl]methyl]-N,N-diethylbenzamide.

In a further embodiment, R may be 3-fluorophenyl; and the compound of formula I may be 4-[(3-aminophenyl)[4-[(3-fluorophenyl)methyl]-1-piperazinyl]methyl]-N,N-diethylbenzamide.

In a further embodiment, R may be 4-fluorophenyl; and the compound of formula I may be 4-[(3-aminophenyl)[4-[(4-fluorophenyl)methyl]-1-piperazinyl]methyl]-N,N-diethylbenzamide.

More particularly, the compounds of the present invention and intermediates used for the preparation thereof can be prepared according to the synthetic routes as exemplified in Schemes 1 and 2.

Scheme 1

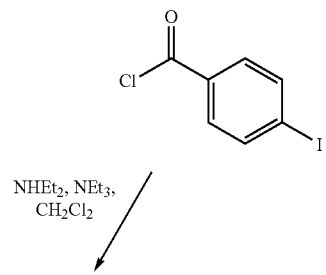

NHEt$_2$, NEt$_3$, CH$_2$Cl$_2$

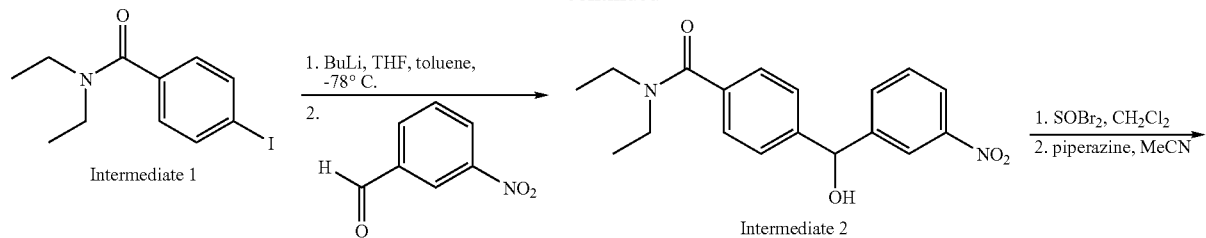
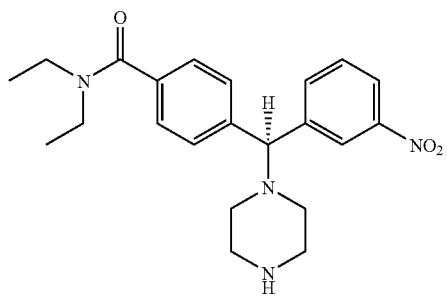
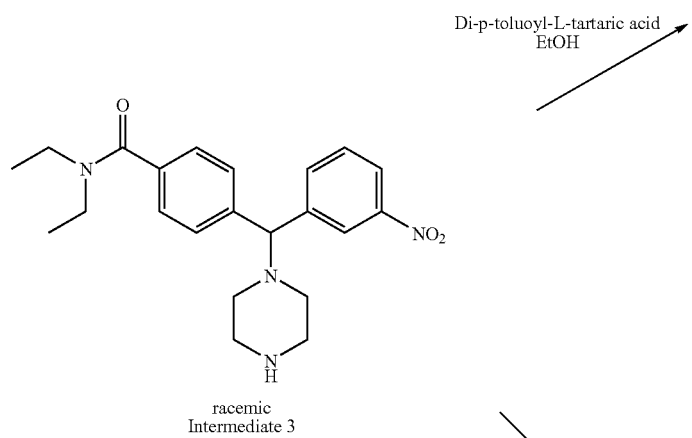
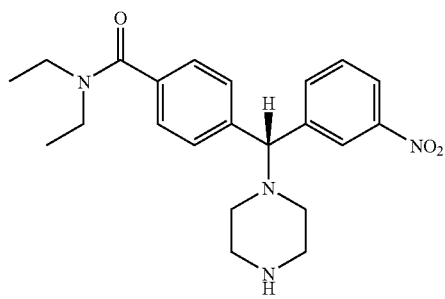

Scheme 2

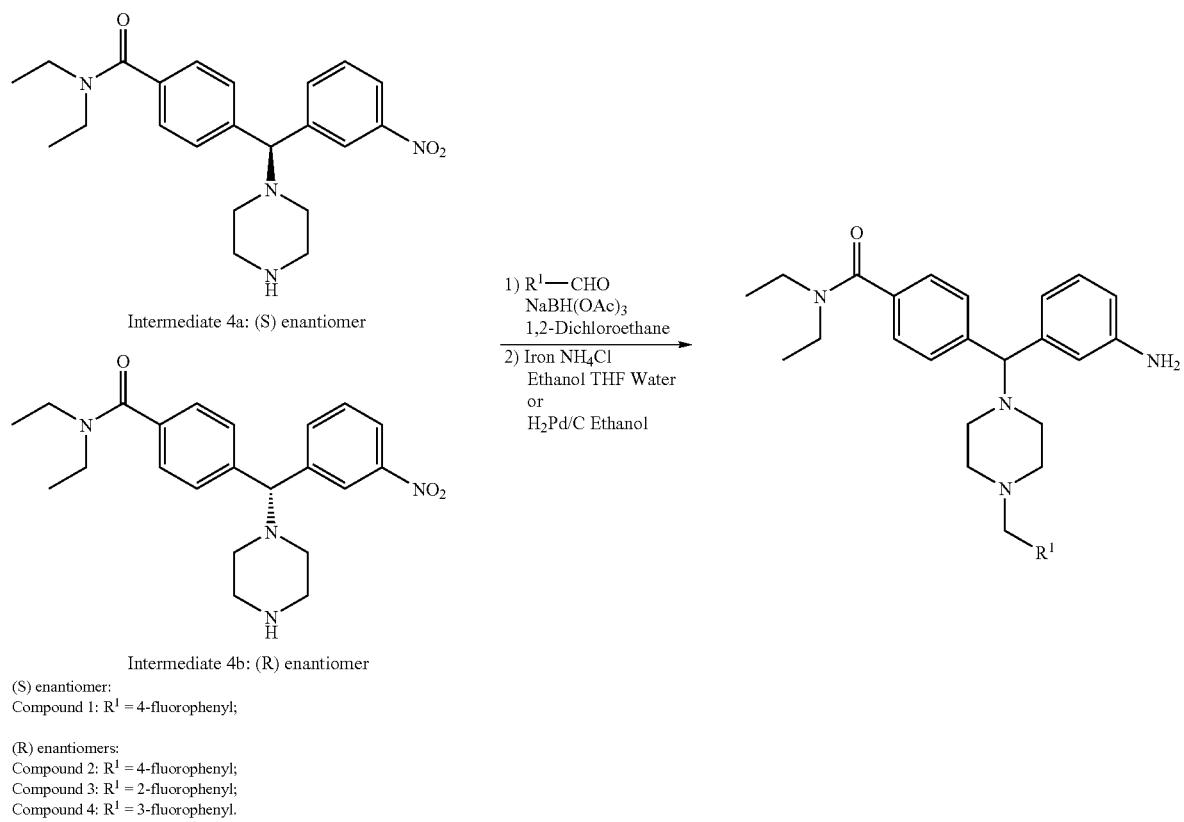

Intermediate 4a: (S) enantiomer

Intermediate 4b: (R) enantiomer (S) enantiomer:
Compound 1: $R^1$ = 4-fluorophenyl;

(R) enantiomers:
Compound 2: $R^1$ = 4-fluorophenyl;
Compound 3: $R^1$ = 2-fluorophenyl;
Compound 4: $R^1$ = 3-fluorophenyl.

BIOLOGICAL EVALUATION AND PROPERTIES

The compounds of the invention are found to be active towards δ receptors in warm-blooded animal, e.g., human. Particularly the compounds of the invention are found to be effective δ receptor ligands. In vitro assays, infra, demonstrate these surprising activities, especially with regard to agonists potency and efficacy as demonstrated in the rat brain functional assay and/or the human δ receptor functional assay (low). This feature may be related to in vivo activity and may not be linearly correlated with binding affinity. In these in vitro assays, a compound is tested for their activity toward δ receptors and $IC_{50}$ is obtained to determine the selective activity for a particular compound towards δ receptors. In the current context, $IC_{50}$ generally refers to the concentration of the compound at which 50% displacement of a standard radioactive δ receptor ligand has been observed.

The activities of the compound towards κ and μ a receptors are also measured in a similar assay.

In Vitro Models
Cell Culture

Human 293S cells expressing cloned human κ, δ and μ receptors and neomycin resistance are grown in suspension at 37° C. and 5% $CO_2$ in shaker flasks containing calcium-free DMEM 10% FBS, 5% BCS, 0.1% Pluronic F-68, and 600 μg/ml geneticin.

Rat brains are weighed and rinsed in ice-cold PBS (containing 2.5 mM EDTA, pH 7.4). The brains are homogenized with a polytron for 30 sec (rat) in ice-cold lysis buffer (50 mM Tris, pH 7.0, 2.5 mM EDTA, with phenylmethylsulfonyl fluoride added just prior use to 0.5 MmM from a 0.5M stock in DMSO:ethanol).

Membrane Preparation

Cells are pelleted and resuspended in lysis buffer (50 mM Tris, pH 7.0, 2.5 mM EDTA, with PMSF added just prior to use to 0.1 mM from a 0.1 M stock in ethanol), incubated on ice for 15 min, then homogenized with a polytron for 30 sec. The suspension is spun at 1000 g (max) for 10 min at 4° C. The supernatant is saved on ice and the pellets resuspended and spun as before. The supernatants from both spins are combined and spun at 46,000 g (max) for 30 min. The pellets are resuspended in cold Tris buffer (50 mM Tris/Cl, pH 7.0) and spun again. The final pellets are resuspended in membrane buffer (50 mM Tris, 0.32 M sucrose, pH 7.0). Aliquots (1 ml) in polypropylene tubes are frozen in dry ice/ethanol and stored at −70° C. until use. The protein concentrations are determined by a modified Lowry assay with sodium dodecyl sulfate.

Binding Assays

Membranes are thawed at 37° C., cooled on ice, (or kept on ice if not used immediately) passed 3 times through a 25-gauge needle, and diluted into binding buffer (50 mM Tris, 3 mM $MgCl_2$, 1 mg/ml BSA (Sigma A-7888), pH 7.4, which is stored at 4° C. after filtration through a 0.22 m filter, and to which has been freshly added 5 μg/ml aprotinin, 10 μM bestatin, 10 μM diprotin A if the membranes are derived from tissue (rat, mouse, monkey, no DTT). Aliquots of 100 μl are added to iced 12×75 mm polypropylene tubes containing 100 μl of the appropriate radioligand and 100 μl of test compound at various concentrations. Total (TB) and nonspecific (NS) binding are determined in the absence and presence of 10 μM naloxone respectively. The tubes are vortexed and incubated at 25° C. for 60-75 min, after which time the contents are rapidly vacuum-filtered and washed with about 12 ml/tube iced wash buffer (50 mM Tris, pH 7.0, 3 mM MgCl$_2$) through GF/B filters (Whatman) presoaked for at least 2 h in 0.1% polyethyleneimine. The radioactivity (dpm) retained on the filters is measured with a beta counter after soaking the filters for at least 12 h in minivials containing 6-7 ml scintillation fluid. If the assay is set up in 96-place deep well plates, the filtration is over 96-place PEI-soaked unifilters, which are washed with 3×1 ml wash buffer, and dried in an oven at 55° C. for 2 h. The filter plates are counted in a TopCount (Packard) after adding 50 µl MS-20 scintillation fluid/well. In the case of assays performed in 96 deep well plates, the IC$_{50}$ of compounds are evaluated from 10-point displacement curves in the case of Delta, and 5-point displacement curves in the case of Mu and Kappa. The assay is done in 300 µl with the appropriate amount of membrane protein (2 µg, 35 µg, and 1 µg, in the case of Delta, Mu, and Kappa, respectively) and 50000-80000 dpm/well of the appropriate tracer (125I-Deltorphin II, 125I-FK33824, and 125I-DPDYN for Delta, Mu, and Kappa, respectively). The total binding and non-specific binding are determined in absence and presence of 10 µM of Naloxone.

Functional Assays

The agonist activity of the compounds is measured by determining the degree to which the compounds receptor complex activates the binding of GTP to G-proteins to which the receptors are coupled. In the GTP binding assay, GTP[γ]$^{35}$S is combined with test compounds and membranes from HEK-293S cells expressing the cloned human opioid receptors or from homogenised rat or mouse brain. Agonists stimulate GTP[γ]$^{35}$S binding in these membranes. The EC$_{50}$ and E$_{max}$ values of compounds are determined from dose-response curves. Right shifts of the dose response curve by the delta antagonist naltrindole are performed to verify that agonist activity is mediated through delta receptors. For human δ receptor functional assays, EC$_{50}$ (low) is measured when the human δ receptors used in the assay were expressed at lower levels in comparison with those used in determining EC$_{50}$ (high). The E$_{max}$ values were determined in relation to the standard δ agonist SNC80, i.e., higher than 100% is a compound that has better efficacy than SNC80.

Procedure for Rat Brain GTP

Rat brain membranes are thawed at 37° C., passed 3 times through a 25-gauge blunt-end needle and diluted in the GTPγS binding (50 mM Hepes, 20 mM NaOH, 100 mM NaCl, 1 mM EDTA, 5 mM MgCl$_2$, pH 7.4, Add fresh: 1 mM DTT, 0.1% BSA). 120 µM GDP final is added membranes dilutions. The EC$_{50}$ and Emax of compounds are evaluated from 10-point dose-response curves done in 300 µl with the appropriate amount of membrane protein (20n/well) and 100000-130000 dpm of GTPγ$^{35}$S per well (0.11-0.14 nM). The basal and maximal stimulated binding are determined in absence and presence of 3 µM SNC80. The assay performed on HEK 293S cells stably expressing cloned Delta receptors is done in a slightly different buffer (50 mM Hepes, 20 mM NaOH, 200 mM NaCl, 1 mM EDTA, 5 mM MgCl$_2$, pH 7.4, Add fresh: 0.5% BSA, no DTT) and with a 3 µM final conc. of GDP.

Data Analysis

The specific binding (SB) was calculated as TB-NS, and the SB in the presence of various test compounds was expressed as percentage of control SB. Values of IC$_{50}$ and Hill coefficient (n$_H$) for ligands in displacing specifically bound radioligand were calculated from logit plots or curve fitting programs such as Ligand, GraphPad Prism, SigmaPlot, or ReceptorFit. Values of K$_i$ were calculated from the Cheng-Prussoff equation. Mean±S.E.M. values of IC$_{50}$, K$_i$ and n$_H$ were reported for ligands tested in at least three displacement curves.

Table 1 shows some the biological data of certain compounds of the invention measured using the above described assays.

| Structure | IC50$_{hd}$ | IC50$_{hk}$ | IC50$_{hm}$ | EC50$_h$ (low) | EC50$_h$ (low) Emax | EC50$_h$ (high) | EC50$_h$ (high) Emax | EC50$_{rb}$ | EC50$_{rb}$ Emax |
|---|---|---|---|---|---|---|---|---|---|
| Compound 2 | 0.587 | 5524 | 715 | 20.63 | 95.3 | 4.18 | 103.8 | 22.82 | 130.3 |
| Compound 1 | 8.80 | >10000 | 3316 | N/A | N/A | 100.3 | 89.09 | 465.9 | 66.32 |
| Compound 3 | 0.717 | 7258 | 2262 | 48.10 | 89.96 | N/A | N/A | N/A | N/A |
| Compound 4 | 1.08 | 5767 | 2736 | 77.42 | 84.44 | N/A | N/A | N/A | N/A |

N/A: not available

Receptor Saturation Experiments

Radioligand K$_δ$ values are determined by performing the binding assays on cell membranes with the appropriate radioligands at concentrations ranging from 0.2 to 5 times the estimated K$_δ$ (up to 10 times if amounts of radioligand required are feasible). The specific radioligand binding is expressed as pmole/mg membrane protein. Values of K$_δ$ and B$_{max}$ from individual experiments are obtained from nonlinear fits of specifically bound (B) vs. nM free (F) radioligand from individual according to a one-site model.

Determination of Mechano-Allodynia Using Von Frey Testing

Testing is performed between 08:00 and 16:00 h using the method described by Chaplan et al. (1994). Rats are placed in Plexiglas cages on top of a wire mesh bottom which allows access to the paw, and are left to habituate for 10-15 min. The area tested is the mid-plantar left hind paw, avoiding the less sensitive foot pads. The paw is touched with a series of 8 Von Frey hairs with logarithmically incremental stiffness (0.41, 0.69, 1.20, 2.04, 3.63, 5.50, 8.51, and 15.14 grams; Stoelting, Ill., USA). The von Frey hair is applied from underneath the mesh floor perpendicular to the plantar surface with sufficient force to cause a slight buckling against the paw, and held for approximately 6-8 seconds. A positive response is noted if the paw is sharply withdrawn. Flinching immediately upon removal of the hair is also considered a positive response. Ambulation is considered an ambiguous response, and in such cases the stimulus is repeated.

Testing Protocol

The animals are tested on postoperative day 1 for the FCA-treated group. The 50% withdrawal threshold is determined using the up-down method of Dixon (1980). Testing is started with the 2.04 g hair, in the middle of the series. Stimuli are always presented in a consecutive way, whether ascending or descending. In the absence of a paw withdrawal response to the initially selected hair, a stronger stimulus is presented; in the event of paw withdrawal, the next weaker stimulus is chosen. Optimal threshold calculation by this method requires 6 responses in the immediate vicinity of the 50% threshold, and counting of these 6 responses begins when the first change in response occurs, e.g. the threshold is first crossed. In cases where thresholds fall outside the range of stimuli, values of 15.14 (normal sensitivity) or 0.41 (maximally allodynic) are respectively assigned. The resulting pattern of positive and negative responses is tabulated using the convention, X=no withdrawal; O=withdrawal, and the 50% withdrawal threshold is interpolated using the formula:

$$50\% \text{ g threshold} = 10^{(Xf+k\delta)}/10{,}000$$

where $Xf$=value of the last von Frey hair used (log units); k=tabular value (from Chaplan et al. (1994)) for the pattern of positive/negative responses; and $\delta$=mean difference between stimuli (log units). Here $\delta$=0.224.

Von Frey thresholds are converted to percent of maximum possible effect (% MPE), according to Chaplan et al. 1994. The following equation is used to compute % MPE:

% MPE=Drug treated threshold(g)−allodynia threshold(g)×100Control threshold(g)−allodynia threshold(g)

Administration of Test Substance

Rats are injected (subcutaneously, intraperitoneally, intravenously or orally) with a test substance prior to von Frey testing, the time between administration of test compound and the von Frey test varies depending upon the nature of the test compound.

Writhing Test

Acetic acid will bring abdominal contractions when administered intraperitoneally in mice. These will then extend their body in a typical pattern. When analgesic drugs are administered, this described movement is less frequently observed and the drug selected as a potential good candidate.

A complete and typical Writhing reflex is considered only when the following elements are present: the animal is not in movement; the lower back is slightly depressed; the plantar aspect of both paws is observable. In this assay, compounds of the present invention demonstrate significant inhibition of writhing responses after oral dosing of 1-100 μmol/kg.

(i) Solutions Preparation

Acetic acid (AcOH): 120 μL of Acetic Acid is added to 19.88 ml of distilled water in order to obtain a final volume of 20 ml with a final concentration of 0.6% AcOH. The solution is then mixed (vortex) and ready for injection.

Compound (drug): Each compound is prepared and dissolved in the most suitable vehicle according to standard procedures.

(ii) Solutions Administration

The compound (drug) is administered orally, intraperitoneally (i.p.), subcutaneously (s.c.) or intravenously (i.v.)) at 10 ml/kg (considering the average mice body weight) 20, 30 or 40 minutes (according to the class of compound and its characteristics) prior to testing. When the compound is delivered centrally: Intraventricularly (i.c.v.) or intrathecally (i.t.) a volume of 5 μL is administered.

The AcOH is administered intraperitoneally (i.p.) in two sites at 10 ml/kg (considering the average mice body weight) immediately prior to testing.

(iii) Testing

The animal (mouse) is observed for a period of 20 minutes and the number of occasions (Writhing reflex) noted and compiled at the end of the experiment. Mice are kept in individual "shoe box" cages with contact bedding. A total of 4 mice are usually observed at the same time: one control and three doses of drug.

For the anxiety and anxiety-like indications, efficacy has been established in the geller-seifter conflict test in the rat.

For the functional gastrointestina disorder indication, efficacy can be established in the assay described by Coutinho S V et al, in American Journal of Physiology—Gastrointestinal & Liver Physiology. 282(2):G307-16, 2002 February, in the rat.

ADDITIONAL IN VIVO TESTING PROTOCOLS

Subjects and Housing

Naïve male Sprague Dawley rats (175-200 g) are housed in groups of 5 in a temperature controlled room (22° C., 40-70% humidity, 12-h light/dark). Experiments are performed during the light phase of the cycle. Animals have food and water ad libitum and are sacrificed immediately after data acquisition.

Sample

Compound (Drug) testing includes groups of rats that do not receive any treatment and others that are treated with E. coli lipopolysaccharide (LPS). For the LPS-treated experiment, four groups are injected with LPS, one of the four groups is then vehicle-treated whilst the other three groups are injected with the drug and its vehicle. A second set of experiments are conducted involving five groups of rats; all of which receive no LPS treatment. The naïve group receives no compound (drug) or vehicle; the other four groups are treated with vehicle with or without drug. These are performed to determine anxiolytic or sedative effects of drugs which can contribute to a reduction in USV.

Administration of LPS

Rats are allowed to habituate in the experimental laboratory for 15-20 min prior to treatment. Inflammation is induced by administration of LPS (endotoxin of gram-negative E. coli bacteria serotype 0111:B4, Sigma). LPS (2.4 μg) is injected intracerebro-ventricularly (i.c.v.), in a volume of 10 μl, using standard stereotaxic surgical techniques under isoflurane anaesthesia. The skin between the ears is pushed rostrally and a longitudinal incision of about 1 cm is made to expose the skull surface. The puncture site is determined by the coordinates 0.8 mm posterior to the bregma, 1.5 mm lateral (left) to the lambda (sagittal suture), and 5 mm below the surface of the skull (vertical) in the lateral ventricle. LPS is injected via a sterile stainless steel needle (26-G ⅜) of 5 mm long attached to a 100-μl Hamilton syringe by polyethylene tubing (PE20; 10-15 cm). A 4 mm stopper made from a cut needle (20-G) is placed over and secured to the 26-G needle by silicone glue to create the desired 5 mm depth.

Following the injection of LPS, the needle remains in place for an additional 10 s to allow diffusion of the compound, then is removed. The incision is closed, and the rat is returned to its original cage and allowed to rest for a minimum of 3.5 h prior to testing.

Experimental Setup for Air-puff Stimulation

The rats remains in the experimental laboratory following LPS injection and compound (drug) administration. At the time of testing all rats are removed and placed outside the laboratory. One rat at a time is brought into the testing laboratory and placed in a clear box (9×9×18 cm) which is then placed in a sound-attenuating ventilated cubicle measuring 62 (w)×35 (d)×46 (h) cm (BRS/LVE, Div. Tech-Serv Inc). The delivery of air-puffs, through an air output nozzle of 0.32 cm, is controlled by a system (AirStim, San Diego Intruments) capable of delivering puffs of air of fixed duration (0.2 s) and fixed intensity with a frequency of 1 puff per 10 s.

A maximum of 10 puffs are administered, or until vocalisation starts, which ever comes first. The first air puff marks the start of recording.

Experimental Setup for and Ultrasound Recording

The vocalisations are recorded for 10 minutes using microphones (G.R.A.S. sound and vibrations, Vedbaek, Denmark) placed inside each cubicle and controlled by LMS (LMS CADA-X 3.5B, Data Acquisition Monitor, Troy, Mich.) software. The frequencies between 0 and 32000 Hz are recorded, saved and analysed by the same software (LMS CADA-X 3.5B, Time Data Processing Monitor and UPA (User Programming and Analysis)).

Compounds (Drugs)

All compounds (drugs) are pH-adjusted between 6.5 and 7.5 and administered at a volume of 4 ml/kg. Following compound (drug) administration, animals are returned to their original cages until time of testing.

Analysis

The recording is run through a series of statistical and Fourier analyses to filter (between 20-24 kHz) and to calculate the parameters of interest. The data are expressed as the mean±SEM. Statistical significance is assessed using T-test for comparison between naive and LPS-treated rats, and one way ANOVA followed by Dunnett's multiple comparison test (post-hoc) for drug effectiveness. A difference between groups is considered significant with a minimum p value of $\leq 0.05$. Experiments are repeated a minimum of two times.

Determination of Thermal Hyperalgesia Using the Hargreaves Plantar Test

Administration of FCA or Carrageenan

Freund's Complete Adjuvant (FCA): SIGMA cat. #F 5881, *Mycabacterium tuberculosis* (H37Ra, ATCC 25177), 1 mg/ml, heat killed, dried, 0.85 ml paraffin, 0.15 ml mannide monooleate. Or carrageenan Lambda type IV(Cg): SIGMA cat. #C-3889, (Gelatin, vegetable; Irish moss), (1.0% solution) in NaCl.

Injections are done with a Hamilton syringe with a sterile needle size 26G⅝". Rats are handled and placed in chamber for anaesthesia with isoflurane. When the desired effect is reached, the rat is removed and placed on ventral decubitus (sternal position). The left hind paw is grasped and the needle is introduced subcutaneous, ventral aspect, between footpad of finger #2 and #3 in order the reach the middle of the paw (metatarsal area). Finally, a volume of 100 µl FCA, or 100 µl of carrageenan solution, is slowly injected into the paw, and a small pressure is applied for 3-4 seconds after removal of needles.

If the animals are waking up during the procedure, they are then return in the inhalation chamber until desired effect is reached.

After the intraplantar injection, the animals are allowed to wake up under observation in their cage.

For FCA treatment, rats are allowed 48 hours for the development of the inflammatory process. For carrageenan treatment, rats are allowed 3 hours for the development of the inflammatory process. On the morning of the test, rats are placed in the lab (in their cages). They are allowed to habituate to the room for at least 30 minutes.

Test Site

The heat stimulus is applied to the center of the plantar surface, in between the pads. The test site must be in contact with the glass, with no urine or feces in between, in order to maintain the correct heat transfer properties from the glass to the skin.

The plantar apparatus consists of a box with a glass top/platform, the glass surface is maintained at 30° C. by an internal feedback mechanism. Underneath this glass platform is a light bulb mounted on a moveable arm, a mirror is placed underneath to allow the light to be positioned under the rat's paw. When the light is activated it shines through an aperture of ~2 mm diameter. The experimenter activates the light, and automatic sensors turn the light off when the paw is removed; a cut-off of 20.48 seconds ensures that no tissue damage will occur should the rat fail to remove his paw. The experimenter may also turn off the light at any point. A Timer will record the duration of time that the light is activated.

Flux meter: measures the flux/cm2 when the light is activated. This should be maintained at ~97-98; the flux can be modified by adjusting the plantar device, but must never be changed in the middle of an experiment.

Time-Course

The experiment can be performed after varying lengths of time following the induction of inflammation. Hyperalgesia is measured at 48 h post-FCA injection or 3 h post-carrageenan injection.

Test Procedure

Naïve rats: For the procedure of establishing a Dose Response Curve, one group of 7 rats is used as a control group; they are anesthetised with the remaining 28 rats, but are not given any injection. Testing of the naive group may be done either prior to beginning or immediately following the experiment, with the minimum stress possible, the rats are placed in individual Plexiglas boxes (14×21×9 cm) on top of the plantar device; they are allowed to habituate for a period of 30 minutes. When the animals are ready to test, the light is placed directly under the test-site and activated, and the latency to withdrawal is recorded. After a period of 5-8 minutes, to allow skin temperature to return to normal, a second reading is taken, and the rats are then removed and replaced in their cage.

Baseline Values The remaining 28 rats (divided into 4 groups) that have been injected with FCA (or carrageenan) are placed in individual boxes on the machine and allowed to habituate for 30 minutes. The experimenter should verify the degree of inflammation of the paw and check for discoloration. The heat stimulus is placed under the test site, and the latency to withdrawal is recorded; two readings are taken, as above. It is the comparison of these baseline values with those of the naïve animals that establishes whether hyperalgesia is present.

Post-drug testing: Once hyperalgesia is established, the rats are injected with the compound of interest. Each compound is prepared and dissolved in the most suitable vehicle according to standard procedures. The administration route, doses, volume, and time of testing after injection is specific for that compound (or class of compounds). When testing compounds at 20-30 minutes post-injection, such as for i.v. or s.c. injections, rats are placed and allowed to habituate on the plantar apparatus while the drug produces its effect. When testing compounds at 60 minutes or more following the injection, rats are placed back in their original cage with their cage mates. Rats are always replaced in their original cages with their original cage mates to minimize the stress of re-establishing a social structure within a group of rats. 30 min later rats are placed one the plantar and allowed 30 minutes to habituate to the plantar machine. Testing is performed as described above. Two readings are taken.

Criteria for Testing:

The animal must be calm and quiet, yet alert, and in the correct position, with no urine or feces between the skin of the paw and the glass surface of the machine. An animal should not be tested if:

The animal is in locomotion, including sniffing, grooming and exploring.

The animal is sleeping.

The animal is showing obvious signs of stress (tonic immobility, vocalizations, ears flat), unless these are the possible result of a compound side effect and cannot be avoided.

The animal is positioned in such a way that the paw is not in direct contact with the glass (paw resting on top of tail);

The animal's paw is displaying blue coloring as a result of a bad injection. In this case, the animal is rejected from the experiment completely (at the beginning).

When urine or feces are present, the animal is removed, the glass surface is wiped clean, and then the animal is replaced. When the animal is sleeping, or exhibiting tonic immobility, the experimenter may gently move the box or move their hand in front of the box to elicit a short-term attentional behaviour. Close observation of the animal's behaviour should be conducted throughout the test.

Re-Tests:

At any time during the experiment, if the experimenter is not certain that the paw withdrawal response was not a response to the heat stimulus, the animal may be re-tested after 5-8 minutes. This may be due to the animal moving suddenly, or urinating or defecating while the stimulus is being applied.

Acceptable Responses:

Any of the following are considered responses to the heat stimulus

Withdrawal movement of the paw off the glass (often followed by paw licking)

Lateral movement of the body (contralateral for the stimulated paw)

Toes are moving off the glass

The centroplanar (middle paw) aspect of the inflamed paw is removed from the glass.

Analysis

The data are expressed as the mean±SEM. Statistical significance is assessed using T-test for comparison between naive and inflamed rats, and one way ANOVA followed by Dunnett's multiple comparison test (post-hoc) for drug effectiveness. A difference between groups is considered significant with a minimum p value of $\leq 0.05$.

DRUG METABOLISM AND PHARMACOKINETIC PROPERTIES

It was surprisingly found that one or more drug metabolic and pharmacokinetic properties of the compounds are improved due to the fluoro-substitution on the bottom benzyl of the benzyl-piperazinyl moiety of formula I. In one embodiment, it was found that certain reactive metabolites are reduced or eliminated for the compounds of the present invention. In another embodiment, certain compounds of the present invention provides improved bioavailability, which may be resulted from its weak affinity with 2D6 and 3A4 cytochrome P450. The following assays demonstrated one or more of these surprising properties of these compounds.

Microsomal Incubations

A compound of the present invention (10 μM nominal initial concentration) was incubated individually with rat liver microsomes (0.5 mg/ml protein) in 0.1 M $KH_2PO_4$ buffer (pH 7.4) with 5 mM $MgCl_2$ and 5 mM trapping reagent (glutathione (GSH), N-acetylcysteine (NAC), or $CH_3ONH_2$) for 60 min at 37° C. Reactions were initiated by the addition of NADPH (1 mM) and terminated by the addition of an equal volume of acidified (0.1% formic acid in acetonitrile) to the incubation mixture.

Hepatocyte Incubations

A compound of the present invention (10 μM nominal initial concentration) was individually incubated with freshly isolated rat (Sprague Dawley) and cryopreserved dog (Beagle) hepatocytes ($1 \times 10^6$ cells/mL) at pH 7.4 at 37° C. for 1 hour. Hepatocyte incubation mixtures contained Williams E Medium supplemented with 25 mM HEPES, 1% ITS-G solution (Life Technologies, Cat. No. 41400-045), 10 mM HEPES (pH 7.4), and 2 mM L-glutamine. Incubations were terminated by the addition of equal volume of acidified (0.1% formic acid) acetonitrile to the incubation mixture.

LS-MS Analysis

Following protein precipitation, sample supernatants were analysed for metabolites by full scan LC-MS. Molecular weight information was obtained for each metabolite detected. Fragmentation patterns from additional LC-MS/MS experiments were analyzed to help assign structures of primary metabolites.

Instruments

| HPLC | HP 1100 HPLC System (Hewlett Packard, D-76337 Waldbronn, Germany) |
|---|---|
| MS | LCQ (Finnigan Corporation, 355 River Oaks Parkway, San Jose, CA) |

MS Condition (LCQ)

| Source Voltage | 4.5 Kv |
|---|---|
| Capillary Temp | 180° C. |
| Sheath Gas Flow | 80 |
| Aux Gas Flow | 5 |
| Source Type | EPI |
| Ionization Mode | Positive |

HPLC Conditions

| Column | Phenomenex Synergi MAX-RP, 4μ, 2.0 × 150 mm (Phenomenex, Torrance, CA) |
|---|---|
| Mobile Phase | A = 0.1% formic acid in water, B = ACN |
| Flow Rate | 0.2 mL/min |
| Temperature | 45° C. |
| Detection | LCQ mass spectrometer |

Gradient Method

| Time | A | B |
|---|---|---|
| 0 | 90 | 10 |
| 30 | 40 | 60 |
| 30.1 | 10 | 90 |
| 33 | 10 | 90 |
| 33.1 | 90 | 10 |
| 40 | 90 | 10 |

Testing Results

The primary biotransformation pathways observed for the compounds were N-deethylation, N-dealkylation and hydroxylation. For the compound of the present invention, which has fluoro-substituted benzyl-piperazinyl moiety, no glutathione adduct on the benzene was detected in rat hepatocyte incubates. In contrast, some glutathione adduct on the ring was observed in rat hepatocyte incubates for similar compounds without the fluoro-substituted benzyl ring.

IN VIVO MICRODIALYSIS METHODS

Procedure

Rats are randomly assigned to eight treatment groups: vehicle-quiet, vehicle-stress, drug-quiet, drug-stress. Microdialysis probes (CMA/12, 4 mm membrane length for mPFC) are implanted in the brain 2 hrs before the experiment and are perfused with artificial CSF (aCSF, CMA Microdialysis AB) at a flow rate of 1.1 mL/min. for 2 h to stabilize the baseline. Three 20 min samples are collected to define the baseline, animals are injected ip with vehicle or compounds and sample collection is carried on for the next 5 h. The stress paradigm program is started 20 min after the administration of the compounds. Samples are immediately (on-line) injected on the HPLC systems for analysis of monoamine concentrations. Concentrations of neurotransmitters in 3 samples collected before administration of compounds/vehicle are averaged and defined as baseline (100%). Concentrations of neurotransmitters in the subsequent microdialysates are then expressed as percentage of baseline levels.

Stress Procedure

For the stress procedure, standard passive avoidance boxes, equipped with lights, tone and shockers, are used (Med Associates, Inc). Boxes are placed in sound-attenuating chambers. Stress paradigm occurs over one day. Animals are acclimated to the chambers for 2 hours, then exposed over the course of 6 min to a series of flashing light, followed by electric foot shocks (0.5 sec duration, 1.5 mA intensity, total 10 shocks). "Quiet" group is exposed to chambers with lights, bud does not receive shocks. 40 minutes later animals the light sequence is repeated, but no shocks are administered.

Drug Administration.

All compounds are dissolved in sterile distilled water (Vehicle) and administered intraperitoneally (IP) 20 min prior the stress procedure on day.

HPLC and Electrochemical Detection.

The HPLC system consists of a 5041 pump, Model 5200A Coulochem II detector, MD-150 3×150 mm column, model 5041 Amperometric cell (all from ESA Inc) and on-line injector (From BAS Inc). The mobile phase is: 75 mM Na2HPO4, 25 mM EDTA, 1.7 mM 1-octanesulphonic acid, 100 ul/L triethylamine, 10% acetonitrile, pH 3.0. Potential is set at +0.65V, flow rate is maintained at 0.3 ml/min. Data are collected using a PC-based acquisition/analysis system (501 Computer and A/D Software, ESA, Inc) integrated and transferred into spreadsheet/graphic software for further analysis.

When groups of 6-8 rats, prepared with intracerebral microdialysis probes placed into the medial prefrontal cortex (where the neurochemical signal is strongest) are subjected to the conditioning paradigm described above, increases in norepinepherine (NE) and dopamine are observed in vehicle-treated animals. Certain compounds of the invention block the sustained increase in NE and dopamine Geller-Siefter—Anxiety Model Method In the conflict test, hungry animals are trained to lever-press for food delivery in a standard operant chamber under two conditions. In the first condition, referred to as the unsuppressed component, food is delivered on average after 17 lever-presses are made (also called a VR17 schedule of reinforcement). In the second condition, referred to as the suppressed component and signalled by flashing lights inside the operant chamber, food is also delivered following an average of 17 lever-presses, but electric shock is additionally delivered to the floor of the cage under a separate VR17 schedule. Daily sessions consist of 5 alternating presentations of each component type: suppressed (3 min in duration) and unsuppressed (3 min in duration). The number of lever presses emitted in the suppressed component is obviously low relative to the unsuppressed component. Anti-anxiety agents, such as diazepam, increase the number of lever-presses that the animals will make in the suppressed component within some range of doses, without altering the number of lever presses that are made in the unsuppressed component. Certain compounds of the invention profile as an anxiolytic in this procedure.

EXAMPLES

The invention will further be described in more detail by the following Examples which describe methods whereby compounds of the present invention may be prepared, purified, analyzed and biologically tested, and which are not to be construed as limiting the invention.

Intermediate 1

4-Iodo-N,N-diethylbenzamide

To a mixture of 4-iodo-benzoyl chloride (75 g) in 500 mL $CH_2Cl_2$ was added a mixture of $Et_3N$ (50 mL) and $Et_2NH$ (100 mL) at 0° C. After the addition, the resulting reaction mixture was warmed up to room temperature in 1 hr and was then washed with saturated ammonium chloride. The organic extract was dried ($Na_2SO_4$), filtered and concentrated. Residue was recrystallized from hot hexanes to give 80 g of INTERMEDIATE 1.

Intermediate 2

4-[hydroxy(3-nitrophenyl)methyl]-N,N-diethylbenzamide

N,N-Diethyl-4-iodobenzamide (5.0 g, 16 mmol) was dissolved in THF (150 mL) and cooled to −78° C. under nitrogen atmosphere. n-BuLi (15 mL, 1.07 M solution in hexane, 16 mmol) was added dropwise during 10 min at −65 to −78° C. The solution was then canulated into 3-nitrobenzaldehyde (2.4 g, 16 mmol) in toluene/THF (approx. 1:1, 100 mL) at −78° C. $NH_4Cl$ (aq.) was added after 30 min. After concentration in vacuo, extraction with EtOAc/water, drying ($MgSO_4$) and evaporation of the organic phase, the residue was purified by chromatography on silica (0-75% EtOAc/heptane) to give INTERMEDIATE 2 (2.6 g, 50%). $^1$H NMR (400 MHz, $CDCl_3$) $\delta_H$ 1.0-1.3 (m, 6H), 3.2 (m, 2H), 3.5 (m, 2H), 5.90 (s, 1H), 7.30-7.40 (m, 4H), 7.50 (m, 1H), 7.70 (d, J=8 Hz, 1H), 8.12 (m, 1H), 8.28 (m, 1H).

Intermediate 3

N,N-diethyl-4-[(3-nitrophenyl)(1-piperazinyl)methyl]benzamide

To a solution of alcohol INTERMEDIATE 2 (10.01 g, 30.5 mmol) in dichloromethane (200 mL) was added thionyl bromide (2.58 mL, 33.6 mmol). After one hour at room temperature the reaction was washed with saturated aqueous sodium bicarbonate (100 mL) and the organic layer was separated. The aqueous layer was washed with dichloromethane (3×100 mL) and the combined organic extracts were dried ($Na_2SO_4$), filtered and concentrated.

The crude benzyl bromide was dissolved in acetonitrile (350 mL) and piperazine (10.5 g, 122 mmol) was added. After heating the reaction for one hour at 65° C. the reaction was washed with saturated ammonium chloride/ethyl acetate and the organic layer was separated. The aqueous layer was extracted with ethyl acetate (3×100 mL) and the combined organic extracts were dried ($Na_2SO_4$), filtered and concentrated to give racemic INTERMEDIATE 3.

Intermediate 4b

N,N-diethyl-4-[(R)-(3-nitrophenyl)(1-piperazinyl)methyl]benzamide

Racemic INTERMEDIATE 3 was dissolved in ethanol (150 mL) and di-p-toluoyl-D-tartaric acid (11.79 g, 1 equivalent) was added. The product precipitated out over a 12 hour period. The solid was collected by filtration and was redissolved in refluxing ethanol until all of the solid dissolved (approximately 1200 mL ethanol). Upon cooling the solid was collected by filtration and the recrystallation repeated a second time. The solid was collected by filtration and was treated with aqueous sodium hydroxide (2 M) and was extracted with ethyl acetate. The organic extract was then dried ($Na_2SO_4$), filtered and concentrated to give 1.986 g of INTERMEDIATE 4b.
$^1$H NMR (400 MHz, $CDCl_3$) $\delta_H$ 1.11 (br s, 3H), 1.25 (br s, 3H), 2.37 (br s, 4H), 2.91 (t, J=5 Hz, 4H), 3.23 (br s, 2H), 3.52 (br s, 2H), 4.38 (s, 1H), 7.31-7.33 (m, 2H), 7.41-7.43 (m, 2H), 7.47 (t, J=8 Hz, 1H), 7.75-7.79 (m, 1H), 8.06-8.09 (m, 1H), 8.30-8.32 (m, 1H).
Chiral purity was determined by HPLC using the following conditions:
Chiralpack AD column (Daicel Chemical Industries)
Low rate 1 ml/minute
Run time 30 minutes at 25° C.
Isocratic 15% ethanol (containing 0.1% v/v diethylamine)
85% hexanes (containing 0.1% v/v diethylamine)
Retention time of molecule=20 minutes Intermediate 4a N,N-diethyl-4-[(S)-(3-nitrophenyl)(1-piperazinyl)methyl]benzamide The (S) enantiomer INTERMEDIATE 4a may be obtained by performing the above resolution procedure with di-p-toluoyl-L-tartaric acid.

Compound 1: 4-{(S)-(3-aminophenyl)[4-(4-fluorobenzyl)piperazin-1-yl]methyl}-N,N-diethylbenzamide

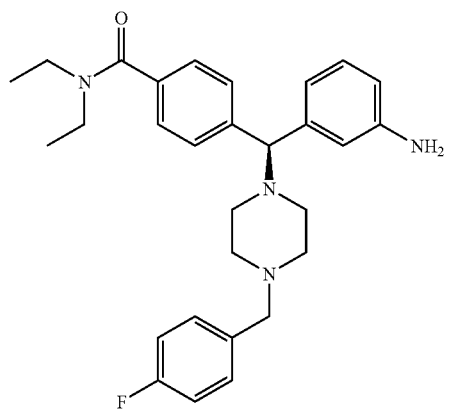

To a solution of INTERMEDIATE 4a (467 mg) in 1,2-dichloroethane (13 ml) was added 4-fluorobenzaldehyde (252 μL; 2 eq) and sodium triacetoxyborohydride (498 mg; 2 eq). The reaction was stirred at room temperature under nitrogen for 18 hours and concentrated. Saturated sodium bicarbonate was added and the aqueous solution was extracted with three portions of dichloromethane and the combined organics were dried over anhydrous sodium sulfate, filtered and concentrated. The compound was dissolved in a mixture of ethanol, tetrahydrofuran, water and saturated ammonium chloride (4 ml; ratios 4:2:1:1 v/v). Iron nanoparticles (3 tips of spatula) were added and the solution was heated at 150° C. for 10 minutes in the microwave. The resulting mixture was cooled, filtered through celite and concentrated. The residue was purified by flash chromatography on silica gel, eluting with a gradient from 1% to 5% MeOH in dichloromethane. The product obtained was dissolved in dichloromethane in which 1.2 mL of 1M HCl in ether was added. Solvent was removed and the product was isolated as the hydrochloride salt to give COMPOUND 1 (164 mg, 30% yield) as a colourless solid. Purity (HPLC): >99%; Optical purity (Chiral HPLC): >99%; $^1$H NMR (400 MHz, $CD_3OD$), 1.08 (t, J=6.5 Hz, 3H), 1.21 (t, J=6.5 Hz, 3H), 3.20-3.26 (m, 4H), 3.51-3.54 (m, 6H), 4.43 (s, 2H), 7.19-7.23 (m, 2H), 7.34 (d, J=8.0 Hz, 1H), 7.40 (d, J=8.0 Hz, 2H), 7.54-7.63 (m, 3H), 7.70-7.82 (m, 4H). Found: C, 54.63; H, 6.49; N, 8.68. $C_{29}H_{36}N_4OF \times 4.1$ HCl×0.8 $H_2O \times 0.1$ $C_4H_{10}O$ has C, 57.67; H, 6.51; N, 8.67%.

Compound 2: 4-{(R)-(3-aminophenyl)[4-(4-fluorobenzyl)piperazin-1-yl]methyl}-N,N-diethylbenzamide

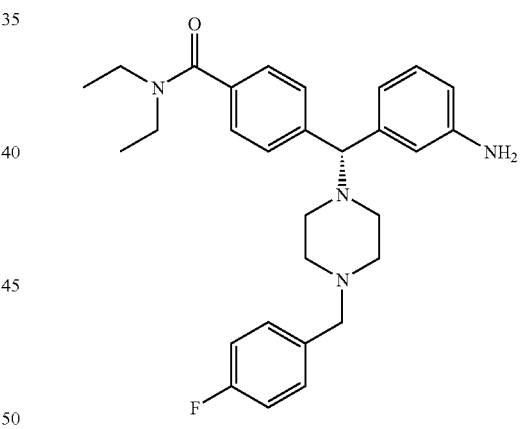

To a solution of INTERMEDIATE 4b (5.790 g, 14.6 mmol) in 1,2-dichloroethane (60 mL) was added 4-fluorobenzaldehyde (2.04 mL, 19.0 mmol) and sodium triacetoxy borohydride (4.02 g, 19.0 mmol). After 20 hours at room temperature the reaction was quenched with aqueous sodium bicarbonate and the organic layer was separated. The aqueous layer was extracted with dichloromethane (3×100 mL) and the combined organic extracts were dried ($Na_2SO_4$), filtered and concentrated. The residue was purified by flash chromatography, eluting 30% to 50% acetone in hexanes to afford a colourless foam (5.285 g, 71%), which is the nitro intermediate. The nitro intermediate (5.285 g, 10.4 mmol) was dissolved in a mixture of ethanol, tetrahydrofuran, water and aqueous saturated ammonium chloride (4:2:1:1 ratio v/v) (100 mL) and granules of iron (0.63 mg, 11.5 mmol) were added. The reaction was heated to reflux and periodically more iron granules were added. After 24 hours at reflux (90° C.) the reaction was cooled to room temperature and filtered through celite and concentrated. To the residue was added aqueous sodium bicarbonate and dichloromethane. The organic layer was separated and the aqueous layer was extracted with dichloromethane (3×100 mL) and the combined organic extracts were dried ($Na_2SO_4$), filtered and concentrated. The product was purified on silica gel, eluting 1% to 5% methanol in dichloromethane to afford COMPOUND 2 (3.505 g) as a pale yellow foam. Impure material was additionally obtained from the above flash chromatography and this was repurified by a second flash chromatography, eluting 100% ethyl acetate to 5% methanol in ethyl acetate to yield a further 0.949 g of COMPOUND 2. Combined material obtained: 4.454 g (90% yield). Purity (HPLC): >99%; Optical purity (Chiral HPLC): >99%; $^1$H NMR (400 MHz, $CD_3OD$), 1.08 (t, J=6.5 Hz, 3H), 1.21 (t, J=6.5 Hz, 3H), 3.20-3.26 (m, 4H), 3.51-3.54 (m, 6H), 4.43 (s, 2H), 7.19-7.23 (m, 2H), 7.34 (d, J=8.0 Hz, 1H), 7.40 (d, J=8.0 Hz, 2H), 7.54-7.63 (m, 3H), 7.70-7.82 (m, 4H). Found: C, 54.00; H, 6.34; N, 8.47. $C_{29}H_{35}FN_4O \times 4.7$ HCl× 0.2 $C_4H_{10}O \times 0.1H_2O$ has C, 54.02; H, 6.37; N, 8.46%.

Compound 3: 4-[(R)-(3-aminophenyl)[4-[(2-fluorophenyl)methyl]-1-piperazinyl]methyl]-N,N-diethyl-benzamide

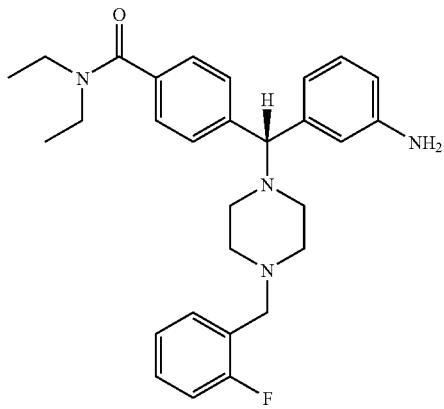

To a solution of INTERMEDIATE 4b (298 mg, 0.752 mmol) in 1,2-dichloroethane (8.5 ml) was added 2-fluorobenzaldehyde (160 mg, 1.503 mmol, 2 eq) and sodium triacetoxyborohydride (319 mg, 1.503 mmol, 2 eq). The reaction was stirred at room temperature under nitrogen for 18 hours and concentrated. Saturated sodium bicarbonate was added and the aqueous solution was extracted with three portions of dichloromethane and the combined organics were dried over anhydrous sodium sulfate, filtered and concentrated. The compound was dissolved in a mixture of ethanol, tetrahydrofuran, water and saturated ammonium chloride (3 ml; ratios 4:2:1:1 v/v). Iron nanoparticles (3 tips of spatula) were added and the solution was heated at 150° C. for 10 minutes in the microwave. The resulting mixture was cooled, filtered through celite and concentrated. The crude was dissolved in $CH_2Cl_2$ and washed with water. The organic layer was separated and the aqueous layer was extracted with dichloromethane. Combined organic extracts were dried ($Na_2SO_4$), filtered and concentrated. The product was purified by reverse phase HPLC (gradient 5-50% $CH_3CN$ in $H_2O$ containing 0.1% TFA) to give COMPOUND 3 (0.28 g, 46% yield) as the TFA salt. This material was lyophilized from $CH_3CN/H_2O$ to produce a pale yellow powder. $^1$H NMR (400 MHz, $CD_3OD$) 1.08 (t, J=6.6 Hz, 3H), 1.22 (t, J=6.6 Hz, 3H), 2.39 (br s, 2H), 3.02 (br s, 2H), 3.18-3.38 (m, 4H), 3.43 (br s, 2H), 3.52 (q, J=6.8 Hz, 2H), 4.43 (s, 2H), 4.53 (s, 1H), 7.09 (dt, J=2.3, 6.8 Hz, 1H), 7.24-7.30 (m, 1H), 7.30-7.41 (m, 6H), 7.52-7.60 (m, 4H). Anal. Calcd for $C_{29}H_{35}FN_4O \times 2.8$ TFA×0.4$H_2O$: C, 51.88; H, 4.86; N, 6.99. Found: C, 51.89; H, 4.89; N, 6.97%. M.S. (calcd): 475.3 (MH+), M.S. (found): 475.2 (MH+). HPLC: k': 2.35; Purity: >99% (215 nm), >99% (254 nm), >99% (280 nm). HPLC Conditions: Zorbax C-18, gradient 10-95% B, flow: 1 mL/min, 25° C., A: 0.1% TFA in $H_2O$, B: 0.1% TFA in MeCN. Rotation: $[\alpha]^{16}_D$=−8.91 (c=1.179, MeOH).

Compound 4 4-[(R)-(3-aminophenyl)[4-[(3-fluorophenyl)methyl]-1-piperazinyl]methyl]-N,N-diethyl-benzamide

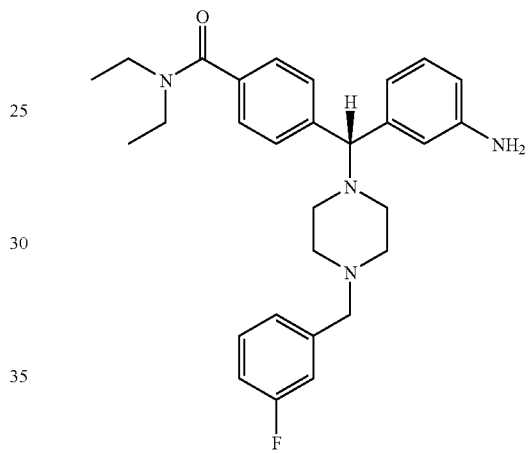

To a solution of INTERMEDIATE 4b (281 mg, 0.709 mmol) in 1,2-dichloroethane (8 ml) was added 3-fluorobenzaldehyde (180 mg, 1.417 mmol, 2 eq) and sodium triacetoxyborohydride (300 mg, 1.417 mmol, 2 eq). The reaction was stirred at room temperature under nitrogen for 18 hours and concentrated. Saturated sodium bicarbonate was added and the aqueous solution was extracted with three portions of dichloromethane and the combined organics were dried over anhydrous sodium sulfate, filtered and concentrated. The product was dissolved in a mixture of ethanol, tetrahydrofuran, water and saturated ammonium chloride (3 ml; ratios 4:2:1:1 v/v). Iron nanoparticles (3 tips of spatula) were added and the solution was heated at 150° C. for 10 minutes in the microwave. The resulting mixture was cooled, filtered through celite and concentrated. The resulting product was dissolved in $CH_2Cl_2$ and washed with water. The organic layer was separated and the aqueous layer was extracted with dichloromethane. Combined organic extracts were dried ($Na_2SO_4$), filtered and concentrated. The product was purified by reverse phase HPLC (gradient 5-50% $CH_3CN$ in $H_2O$ containing 0.1% TFA) to give COMPOUND 4 (0.375 g, 65% yield) as its TFA salt. This material was lyophilized from $CH_3CN/H_2O$ to produce a pale yellow powder. $^1$H NMR (400 MHz, $CD_3OD$) 1.08 (t, J=6.4 Hz, 3H), 1.21 (t, J=6.8 Hz, 3H), 2.38 (br s, 2H), 3.00 (br s, 2H), 3.16-3.28 (m, 4H), 3.40 (br s, 2H), 3.51 (q, J=6.8 Hz, 2H), 4.37 (s, 2H), 4.56 (s, 1H), 7.18 (ddd, J=1.2, 2.3, 7.8 Hz, 1H), 7.24 (ddd, J=1.0, 2.7, 8.8 Hz, 1H), 7.28-7.38 (m, 4H), 7.55 (d, J=8.2 Hz, 2H). Anal. Calcd for $C_{29}H_{35}FN_4O \times 2.7$ TFA×1.1$H_2O$: C, 51.50; H, 5.01; N, 6.98. Found: C, 51.52; H, 5.01; N, 6.87%. M.S. (calcd): 475.3 (MH+), M.S. (found): 475.2 (MH+).

HPLC: k': 2.43; Purity: >99% (215 nm), >99% (254 nm), >99% (280 nm). HPLC Conditions: Zorbax C-18, gradient 10-95% B, flow: 1 mL/min, 25° C., A: 0.1% TFA in $H_2O$, B: 0.1% TFA in MeCN. Rotation: $[\alpha]^{16}_D = -8.94$ (c=1.04, MeOH)

What is claimed is:

1. A method for the treatment of depression in a warm-blooded animal, comprising administering to said animal in need of said treatment a therapeutically effective amount of a compound, (R)-4-((3-aminophenyl)(4-(4-fluorobenzyl)piperazin-1-yl)methyl)-N,N-diethylbenzamide, having the following formula:

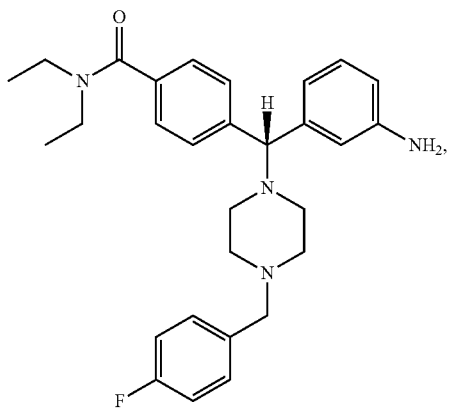

I or a pharmaceutically acceptable salt thereof.

2. A method for the treatment of depression in a warm-blooded animal, comprising administering to said animal in need of said treatment a pharmaceutical composition comprising a therapeutically effective amount of a compound, (R)-4-((3-aminophenyl)(4-(4-fluorobenzyl) piperazin-1-yl) methyl)-N,N-diethylbenzamide, having the following formula:

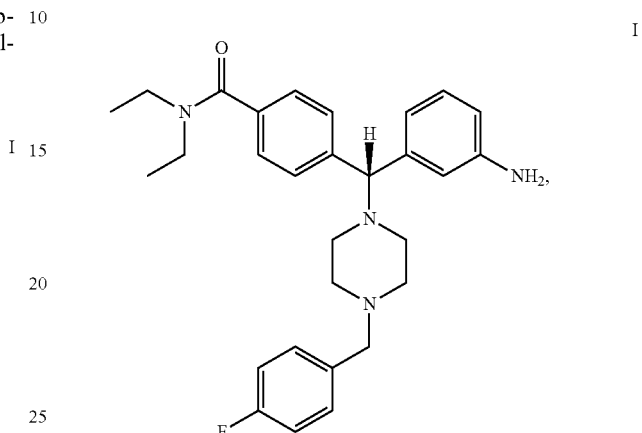

I or a pharmaceutically acceptable salt thereof.

* * * * *